(12) United States Patent
Shahriari et al.

(10) Patent No.: US 11,911,268 B1
(45) Date of Patent: Feb. 27, 2024

(54) TRANSCATHETER DEVICE FOR ENDOVASCULAR AORTIC REPAIR AND METHOD OF USING THE SAME

(71) Applicant: Aortic Innovations, LLC, Hillsboro Beach, FL (US)

(72) Inventors: Ali Shahriari, Hillsboro Beach, FL (US); Justin R. Nifong, Lexington, NC (US)

(73) Assignee: Aortic Innovations, LLC, Hillsboro Beach, FL (US)

( * ) Notice: Subject to any disclaimer, the term of this patent is extended or adjusted under 35 U.S.C. 154(b) by 0 days.

(21) Appl. No.: 17/182,041

(22) Filed: Feb. 22, 2021

Related U.S. Application Data

(60) Provisional application No. 62/978,854, filed on Feb. 20, 2020.

(51) Int. Cl.
| | | |
|---|---|---|
| A61F 2/24 | (2006.01) | |
| A61F 2/07 | (2013.01) | |
| A61F 2/90 | (2013.01) | |
| A61F 2/958 | (2013.01) | |
| A61F 2/962 | (2013.01) | |
| A61F 2/06 | (2013.01) | |

(52) U.S. Cl.
CPC .............. *A61F 2/2418* (2013.01); *A61F 2/07* (2013.01); *A61F 2/2433* (2013.01); *A61F 2/90* (2013.01); *A61F 2/958* (2013.01); *A61F 2/962* (2013.01); *A61F 2002/061* (2013.01); *A61F 2002/075* (2013.01); *A61F 2/2412* (2013.01); *A61F 2210/0076* (2013.01); *A61F 2220/005* (2013.01); *A61F 2250/0015* (2013.01); *A61F 2250/0023* (2013.01); *A61F 2250/0039* (2013.01); *A61F 2250/0051* (2013.01); *A61F 2250/006* (2013.01); *A61F 2250/0069* (2013.01)

(58) Field of Classification Search
CPC .......... A61F 2/07–2002/077; A61F 2/24–2424
See application file for complete search history.

(56) References Cited

U.S. PATENT DOCUMENTS

| | | | | |
|---|---|---|---|---|
| 2004/0111146 | A1* | 6/2004 | McCullagh | A61F 2/07 623/1.13 |
| 2008/0275540 | A1* | 11/2008 | Wen | A61F 2/2418 623/2.38 |
| 2014/0330367 | A1* | 11/2014 | Thapliyal | A61F 2/2415 623/2.11 |
| 2016/0081829 | A1* | 3/2016 | Rowe | A61F 2/954 623/2.37 |
| 2016/0262880 | A1* | 9/2016 | Li | A61F 2/2418 |
| 2017/0312103 | A1* | 11/2017 | Shahriari | A61F 2/89 |
| 2018/0325703 | A1* | 11/2018 | Shahriari | A61F 2/82 |

\* cited by examiner

*Primary Examiner* — Rebecca S Preston
(74) *Attorney, Agent, or Firm* — NK Patent Law

(57) ABSTRACT

A transcatheter valve assembly includes a main body that defines a braided stent frame having a proximal end and a distal end and a graft material covering at least a portion of the braided stent frame. The graft material is coupled to the braided stent frame at each of the proximal end and the distal end. The braided stent frame is configured to modify a length and diameter thereof to fit a diameter of a patient. A medial portion defines one of an open facing surface that is positioned proximal the coronary arteries when the valve assembly is deployed, and a pair of conduits configured for receiving a stent to fluidly engage with the coronary arteries when the valve assembly is deployed. A valve housing is at the proximal end of the transcatheter valve assembly.

5 Claims, 18 Drawing Sheets

TRANSCATHETER DEVICE FOR ENDOVASCULAR AORTIC REPAIR AND METHOD OF USING THE SAME

CROSS-REFERENCE TO RELATED APPLICATIONS

This application claims priority to U.S. Provisional Patent Application No. 62/978,854 entitled TRANSCATHETER DEVICE FOR ENDOVASCULAR AORTIC REPAIR AND METHOD OF USING THE SAME, filed on Feb. 20, 2020, the entire contents of which are incorporated by reference herein.

TECHNICAL FIELD

The present disclosure relates to a device and method of using same for endovascular aortic repair, including repair of aortic valve disease, aortic stenosis, ascending aortic aneurysms, aortic insufficiency, aortic regurgitation, ascending aneurysm, bicuspid valve disease, and/or Type A dissections.

BACKGROUND

The normal aortic root and the ascending aorta are composed of the aortic annulus, the sinuses of Valsalva, the sinutubular junction, and the tubular portion. The challenge facing practitioners of endovascular repair of ascending aortic aneurysms is that there is a very short proximal landing zone at the level of the sinutubular junction, there is variable coronary anatomy from patient to patient, and, in many cases, there is involvement of the aortic valve with either stenosis or insufficiency. Generally speaking, and as discussed in the article SURGERY INSIGHT: THE DILATED ASCENDING AORTA—INDICATIONS FOR SURGICAL INTERVENTION, by James E. Davies and Thralf M. Sundt published in Nature Clinical Practice Cardiovascular Medicine (2007), the contents of which are incorporated herein by reference in its entirety, there are three basic types of involvement of the ascending aorta, designated as Type A, B, or C. These will be discussed in further detail below.

Type A aneurysms are most commonly found in younger patients and patients with connective tissue disorders such as Marfan syndrome. The anatomical characteristics of Type A aneurysms are dilatation of the sinuses of Valsalva with or without dilatation of the aortic annulus. The sinutubular junction is most often dilated. The valve could be normal, stenotic or insufficient.

The anatomical characteristics of Type B aneurysms are dilatation of the tubular portion. Initially the sinutubular junction may be normal or mildly dilated, however as the aneurysm grows, it stretches the sinutubular junction and may eventually lead to aortic insufficiency. The valve could be normal, stenotic or insufficient. The bulk of the aneurysm is at the level of the tubular aorta.

The anatomical characteristics of Type C aneurysms are dilatation of the sinuses of Valsalva, sinutubular junction and the tubular portion of the aorta. The valve could be normal, stenotic or insufficient. Type B and C aneurysms are most commonly found in an older group of patients.

There are devices clinically used for endovascular repair of ascending aortic aneurysms. Although transcatheter valves are a clinical reality, none in clinical use have been designed with the purpose of endovascular repair of multiple types of ascending aortic aneurysms. Indeed, a device is needed that can treat different anatomical variations of ascending aortic aneurysms, create effective proximal and distal seal zones within the aorta, and have a durable valve component, but that also allows for future valve re-interventions. A device is also needed that would allow for treatment of different coronary anatomical variations among the patient population, allow future coronary re-intervention, but that also avoids coronary compression, and enables treatment of possible paravalvular leaks.

BRIEF DESCRIPTION OF THE DRAWINGS

Embodiments of the present disclosure will now be described by way of example in greater detail with reference to the attached figures, in which.

DETAILED DESCRIPTION OF THE DRAWINGS

Figure 1:
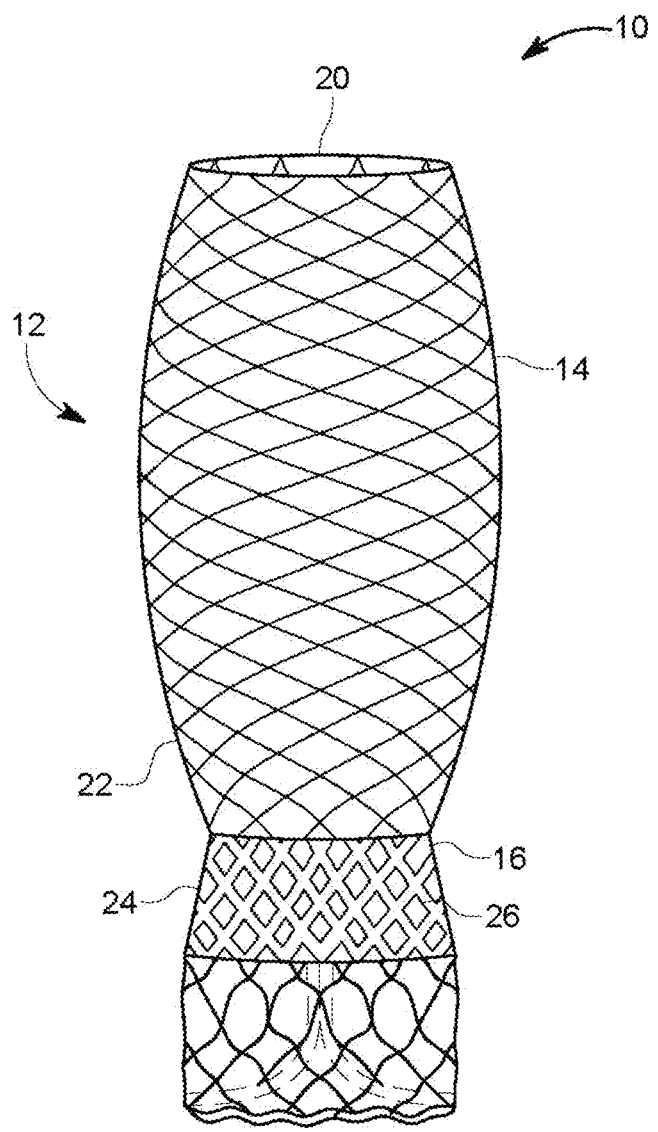
FIG. 1 is a front facing view of a transcatheter valve assembly having a braided construction according to one or more embodiments described herein.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. For example, the term "proximal" refers to the direction that is generally closest to the heart, and the term "distal" refers to the direction that is generally furthest from the heart.

A transcatheter valve assembly is illustrated throughout the figures and generally designated 10. The valve assembly 10 may include a main body 12 as illustrated. The main body 12 may define a braided stent frame 14 having a proximal end 16 and a distal end 20. A graft material 22 covers at least a portion of the braided stent frame 14. The graft material 22 is coupled to the braided stent frame 14 at each of the proximal end 16 and the distal end 20. In this manner, the braided stent frame 14 is configured to modify a length and diameter thereof to fit a diameter of a patient. In other words, since the braided stent frame 14 is coupled to the graft material 22 at the ends, the medial portions of the braided stent frame 14 are able to expand, contract, lengthen, and shorten, and provide some level of arcuity.

Figure 2:
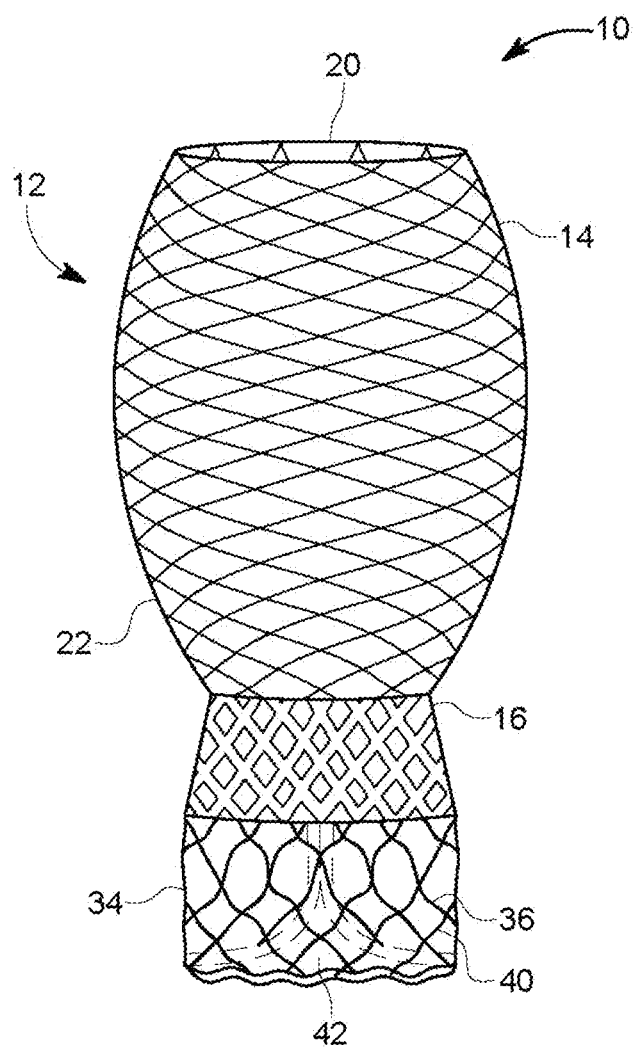
FIG. 2 is a front facing view of a transcatheter valve assembly having a braided construction where the braided portion has been shortened according to one or more embodiments described herein.

Consider, for example, the valve assembly 10 shown in FIG. 2, in which the braided stent frame 14 has been shortened, causing a corresponding widening of the frame 14 material. This could occur, as an example, in response to a larger than average aorta diameter, due to aneurysm or just natural anatomical characteristics. The braided stent frame allows each braided wire to translate relative to adjacent wires and for conformability of the stent frame 14.

The valve assembly 10 may further include a medial portion 24 that defines one of an open facing surface 24 that is positioned proximal the coronary arteries 2 when the valve assembly 10 is deployed, and a pair of conduits 30, each configured for receiving a stent 32 to fluidly engage with the coronary arteries 2 when the valve assembly 10 is deployed. A valve housing 34 is positioned at the proximal end of the transcatheter valve assembly 10.

Figure 3:
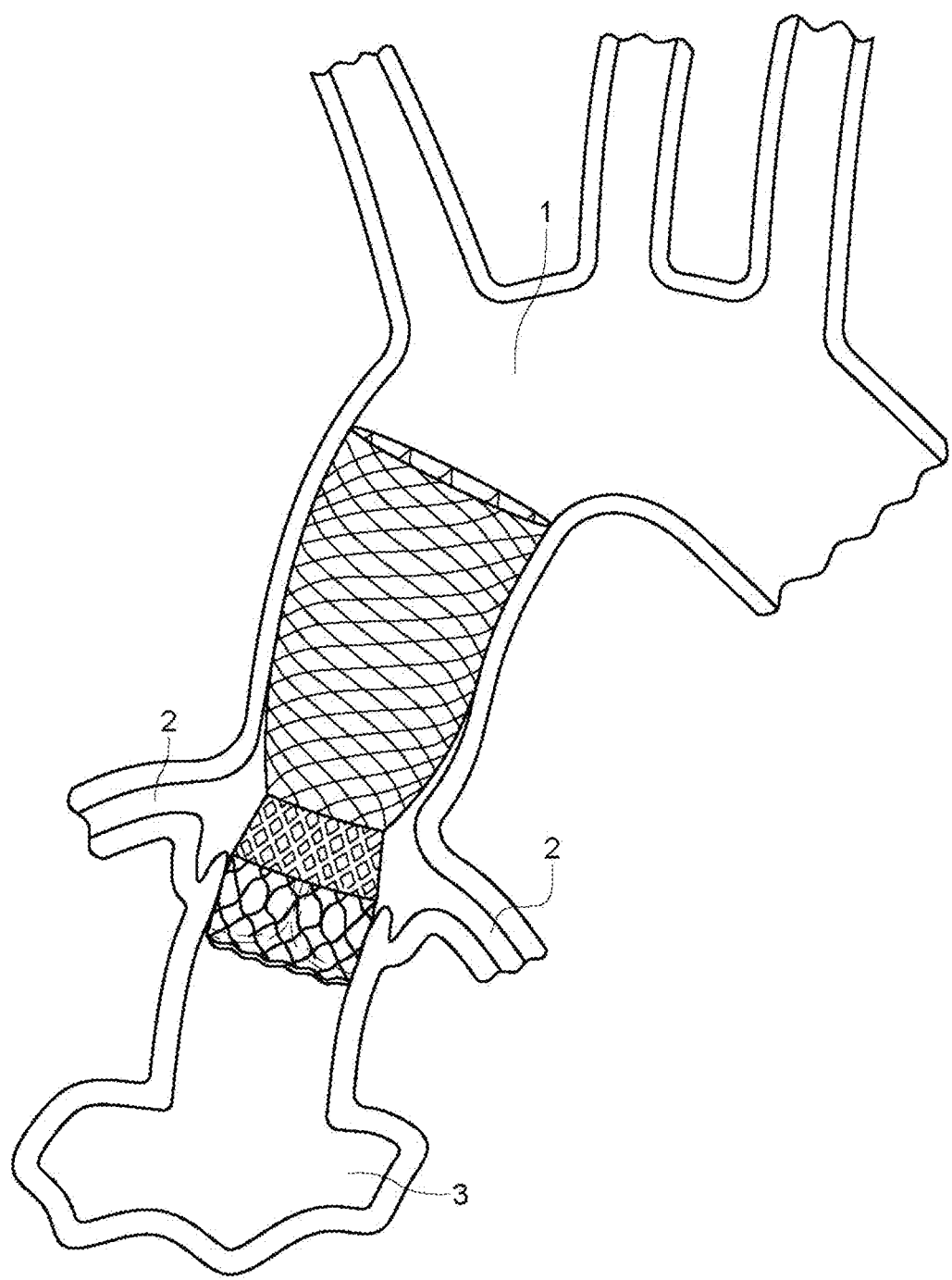
FIG. 3 is a front facing view of a transcatheter valve assembly positioned as a replacement valve within the aorta according to one or more embodiments disclosed herein.
Figure 4:
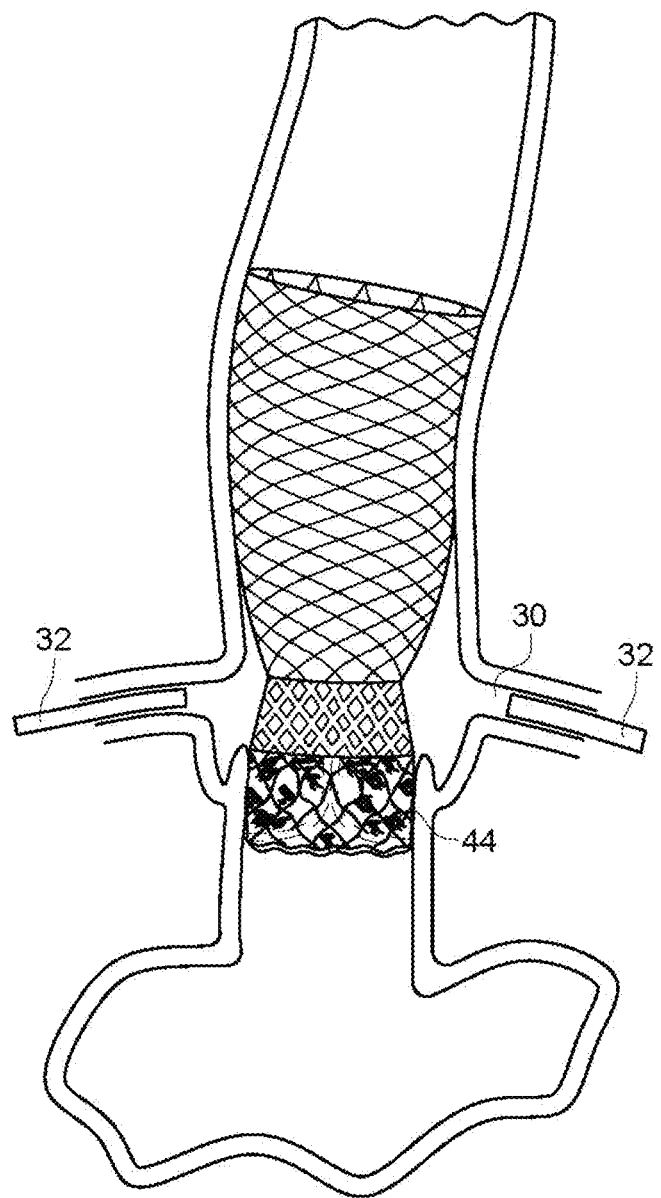
FIG. 4 is a front facing view of a transcatheter valve assembly positioned as a replacement valve within the aorta according to one or more embodiments disclosed herein.
Figure 5:
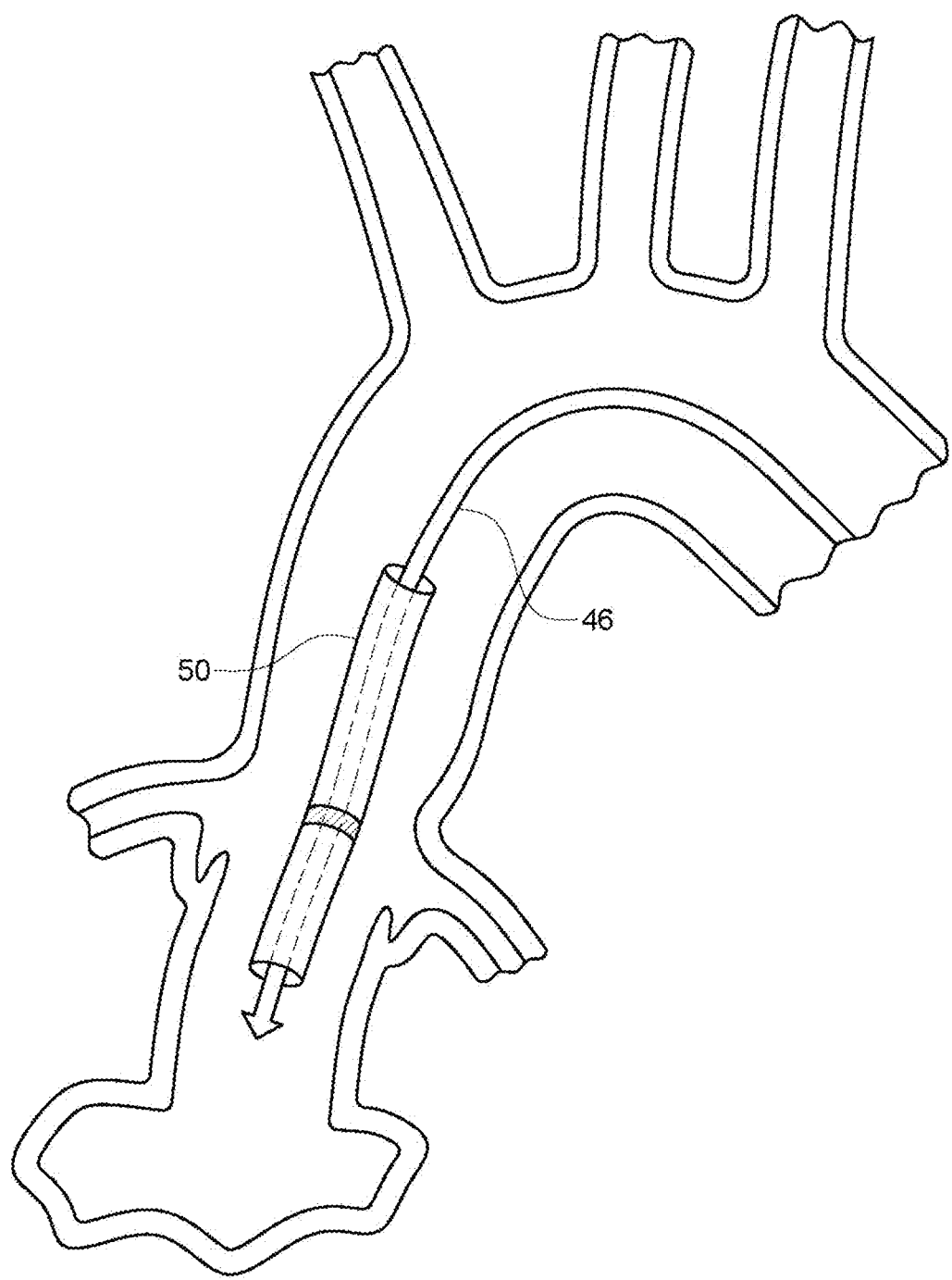
FIG. 5 is a front facing view of a catheter being deployed within an aorta according to one or more embodiments disclosed herein.

In operation, the valve assembly 10 is deployed within the aorta 1 at a position where open surface 24 is opposed to the coronaries, or where conduits 30 and stents 32 provide a stenting to the coronaries 2. The assembly 10 is thus positioned downstream of the aortic chamber 3 as illustrated in FIG. 3.

As illustrated in FIGS. 1 and 2, the braided stent frame 14 comprises a plurality of braided stent wires. These wires are metal wires and may have corrosion resistant and other appropriate properties. The diameter or denier of the wires may vary, as well as the material selection and other characteristics.

In one or more embodiments, the graft material 22 is coupled to the braided stent frame 14 by one or more of stitching, adhesives, crimps, lamination, or other attachment methods. The coupling may be only at each of the proximal and distal ends, may be at one of the proximal and distal ends, or may be along multiple connections points. In one or more embodiments, the graft material 22 covers an entire length of the braided stent frame 14, while in other embodiments, the graft material 22 covers a partial length of the braided stent frame 14, meaning a portion of the stent frame 14 extends outwardly of the graft material 22.

In one or more embodiments as illustrated, the medial portion 24 may define a tapering or reduced diameter to provide clearance external to the valve assembly 10. The tapering and reduced diameter is, however, optional, and may take on many different shapes and configurations.

In one or more embodiments, the valve housing 34 defines a wire frame 36 having a graft material 42 covering thereon. A heart valve 42 may be positioned within the valve housing 34. In this manner, the valve housing 34 may be non-porous to blood flow, and provide a proper sealing surface to seal against the aortic annulus. In one or more embodiments, a plurality of fibers 44 may be provided against the valve housing 34.

In one or more embodiments, the main body 14 is self-expanding. This self-expansion may be due in response to removal of a sheath covering the main body. In this manner, a deployment rod or catheter 46 may pass through a center or the valve assembly 10, and a sheath 50 may be pulled backwards, releasing the valve housing 34 first, then the medial portion 24, and then the main body 12. Alternatively, other means of contracting/expanding the assembly 10 may be employed, such as the valve housing 34 being balloon expandable as an example. Different mechanisms may be used by the operator to effectuate expansion of the various portions/components of the assembly 10.

In operation, the surgeon positions either the open facing surface 24 or the conduits 32 proximal the coronary arteries 1. This may be done through use of radio-opaque markers along the stent or the sheath material. In practice, the valve housing 34 may be deployed first. The surgeon accesses an access artery, such as the femoral artery, positions the assembly 10 and deployment components (46, 50) into place. In one or more embodiments, the valve assembly 10 may also be configured for engaging a second stent positioned in the aorta.

The one or more stent components illustrated herein are for the distal components are created from braided or gridded stents. One of the major benefits of a braided or gridded stent in this application as compared to other stents such as a z-stent or others is that the braided or gridded stent is less likely to create folds and gutters if there is a size mismatch between the device and the aorta thus leading to improved seal between the device and the aortic wall. All valves shown are expandable (either self-expanding or balloon expandable). The components herein may be employed and deployed similar to the device shown in U.S. Pat. No. 8,940,040, incorporated by reference herein.

Figure 6:
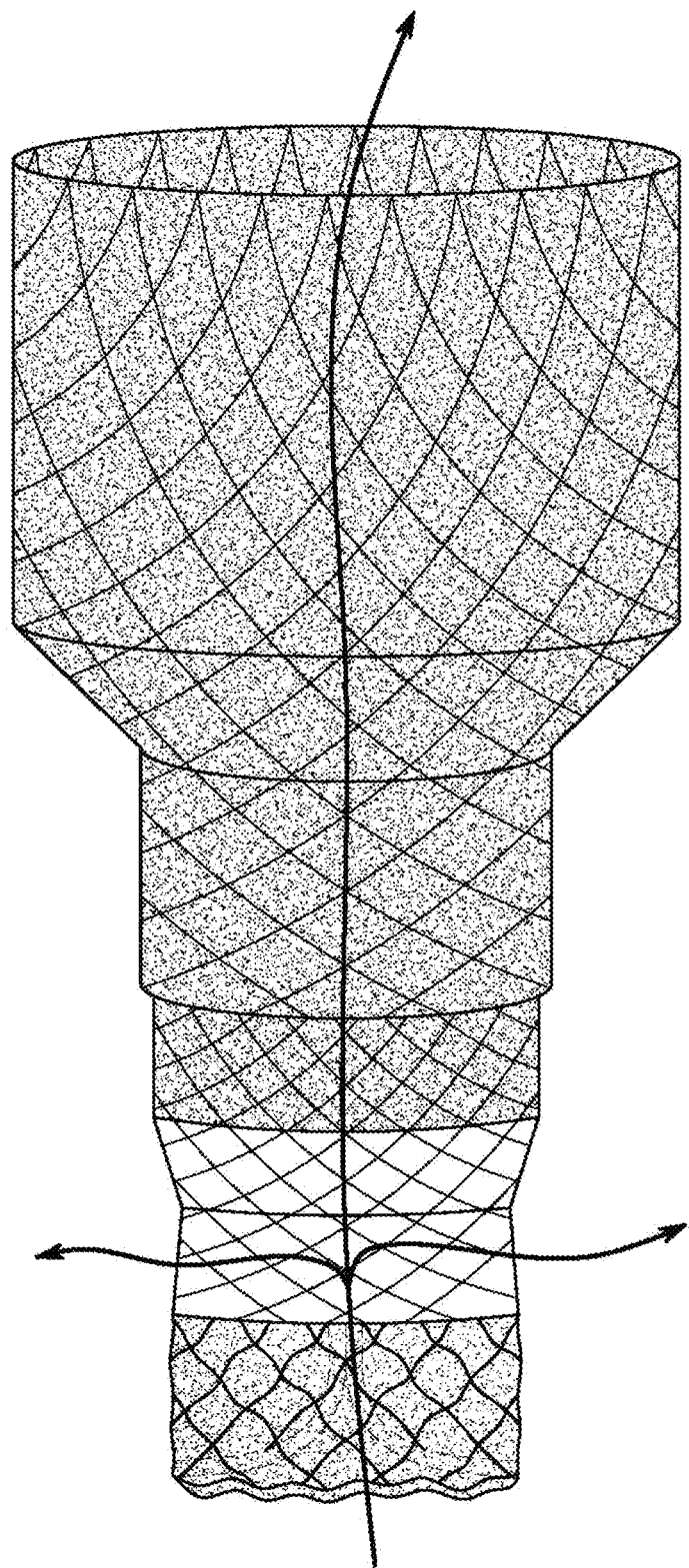
FIG. 6 is a front facing view of a transcatheter valve assembly having a braided construction according to one or more embodiments described herein.

FIG. 6 illustrates a device for treatment of ascending aneurysms or dissections. This is a modular device with the proximal component (red) is partially or totally uncovered and permeable to passage of fluids. The proximal valve bearing component allows for unidirectional passage of fluid from the ventricle of the heart distally into the aorta. The distal component illustrated in FIG. 6 is created of a braided or gridded stent covered with blood and fluid impermeable material such as polyester, PTFE or any other biologically acceptable material. The proximal and distal components interact by sliding into each other and creating a connecting interphase in situ. Alternatively, the components can be mated and secured together during manufacturing as one piece prior to implantation. During implantation, the device is introduced over the wire form through an access vessel and implanted such that the proximal most part of the valve-bearing component attaches to and sealably contacts the aortic annulus and the most distal margin of the distal component seals against the aortic wall at or proximal to the innominate artery. The device can also connect to branched arch devices or other devices implanted in the aortic arch through a sealing sliding interference.

Alternatively, in any of the embodiments disclosed herein, the portions that are covered with a graft material may instead be covered with outwardly extending fibers that provide sealing characteristics for treating an aneurysm, dissection, or just for preventing migration of the stent components. The fibers may be embodied within a single layer of woven materials, or may be multiple layers of fibers, with one forming a base layer for being attached to the wireframe stent, and having a construction that is sufficiently dense to provide sealing characteristics, but not so thick as to cause problems with foreshortening or underexpansion of the stent frame. The various stent frame assemblies disclosed herein may be self-expanding or balloon expandable.

Figure 7:
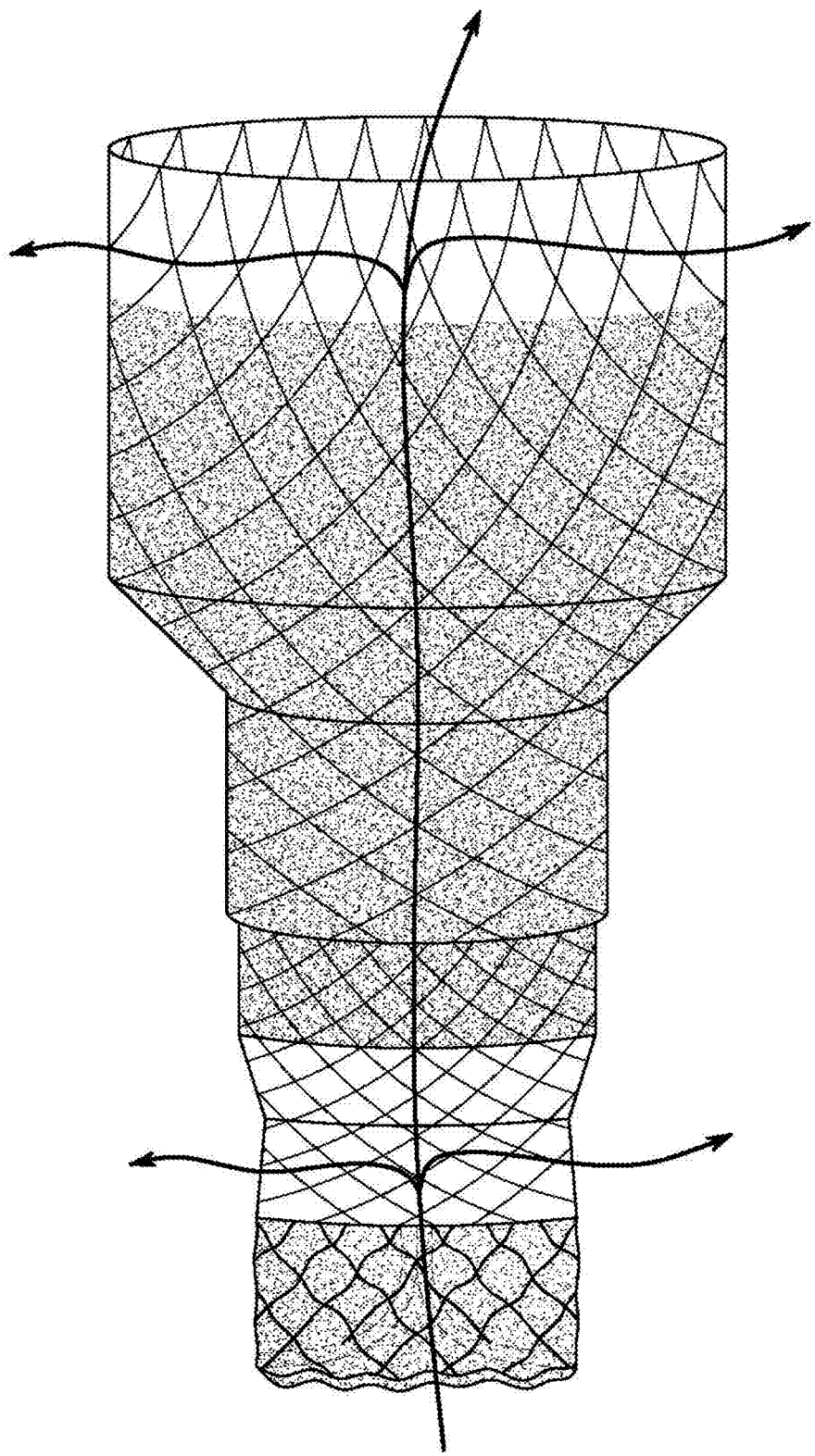
FIG. 7 is a front facing view of a transcatheter valve assembly having a braided construction according to one or more embodiments described herein.

FIG. 7 illustrates a device for treatment of ascending aneurysms or dissections. This is a modular device with the proximal component is partially or totally uncovered and permeable to passage of fluids. The proximal valve bearing component allows for unidirectional passage of fluid from the ventricle of the heart distally into the aorta. The distal component of the embodiment illustrated in FIG. 7 is created of a braided or gridded stent or supporting member at least partially covered with blood and fluid impermeable material such as polyester, PTFE or any other biologically acceptable material. The proximal and distal components interact by sliding into each other and creating a connecting interphase in situ. Alternatively, the components can be mated and secured together during manufacturing as one piece prior to implantation. During implantation, the device is introduced over the wire from an access vessel and implanted such that the proximal most part of the valve-bearing component attaches to and sealably contacts the aortic annulus and the most distal margin of the distal component seals against the aortic wall at or proximal to the innominate artery. The device can also connect to branched arch devices or other devices implanted in the aortic arch through a sealing sliding interference.

Figure 8:
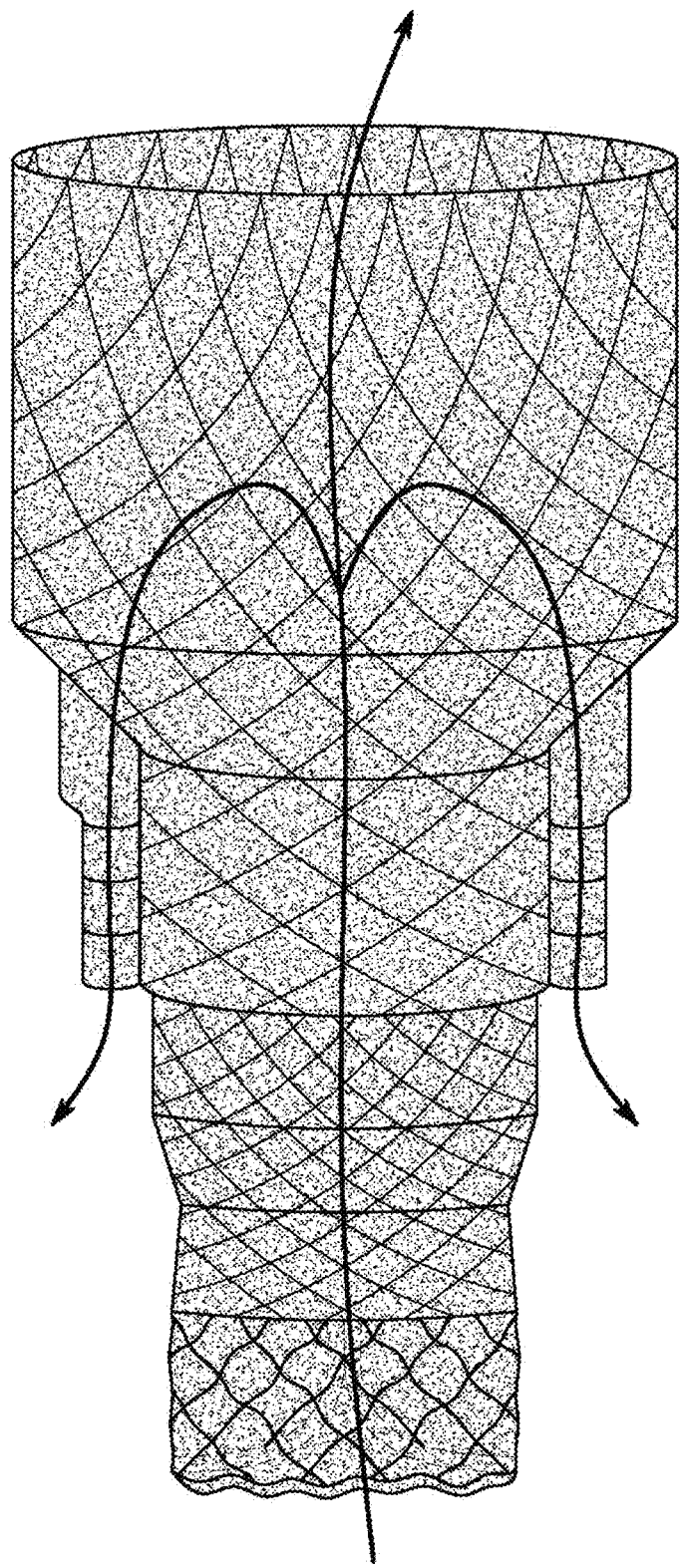
FIG. 8 is a front facing view of a transcatheter valve assembly having a braided construction according to one or more embodiments described herein.

The device illustrated in FIG. 8 shares many of the aspects of the device illustrated in FIG. 7, but the proximal and distal components are both impermeable to blood and fluids. Two conduits alongside the lateral aspect of the distal components, spaced apart 30-180 degrees provide access to and blood supply to the coronary arteries via connecting bridging stents.

Figure 9:
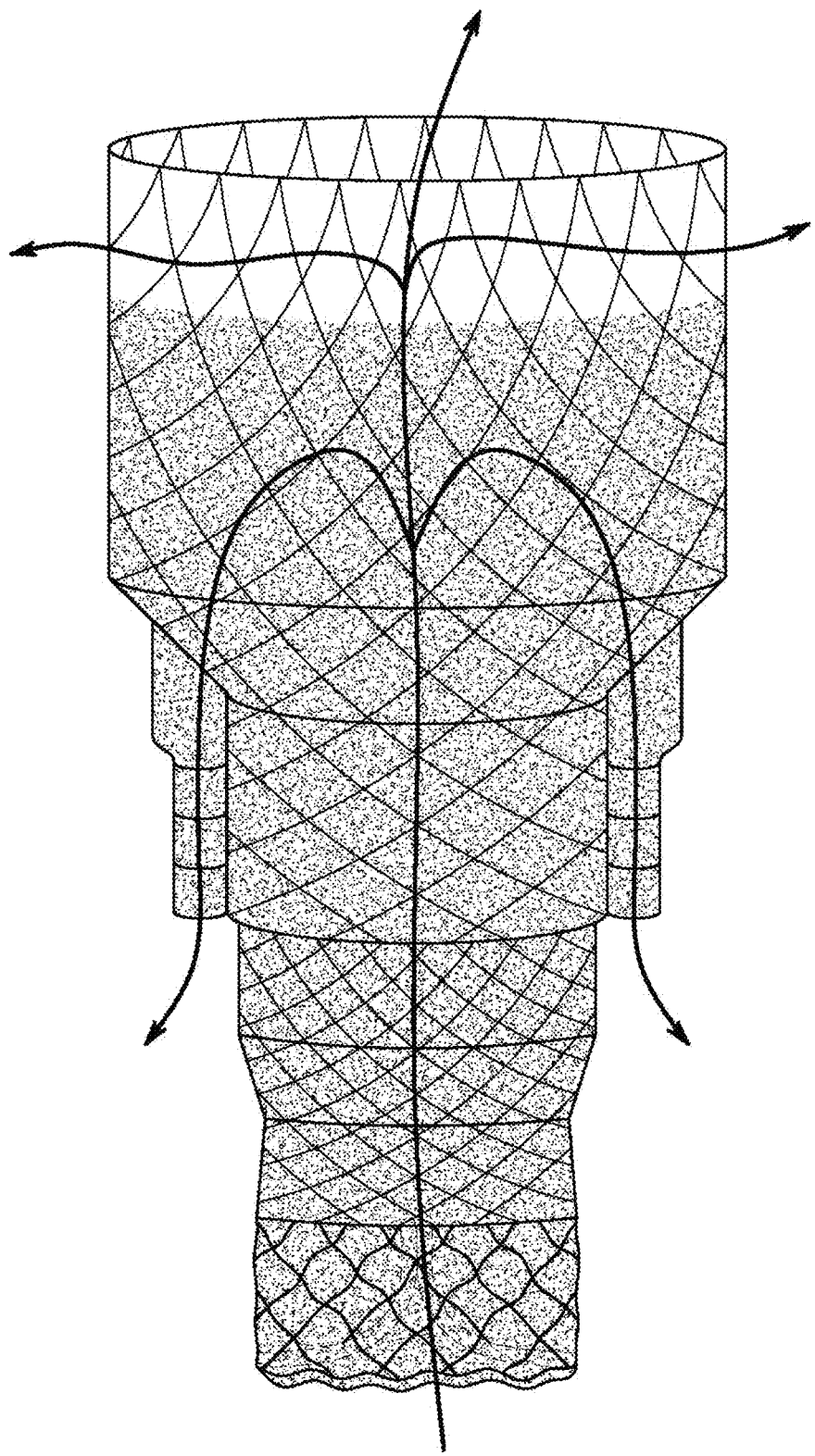
FIG. 9 is a front facing view of a transcatheter valve assembly having a braided construction according to one or more embodiments described herein.

The embodiment illustrated in FIG. 9 shares many characteristics as that shown in FIG. 8, however, the distal component has an uncovered section distal to the covered section. The uncovered section can be placed across the aortic arch to provide stability while maintaining blood flow to the supra-aortic vessels. In this manner, if the uncovered section were to extend beyond the supra-aortic vessels, no blockage would occur. Additionally, in this embodiment, the uncovered portion could define a smaller grid construction that allows for embolic protection to the device to block any large calcified emboli from entering the innominate artery.

Figure 10:
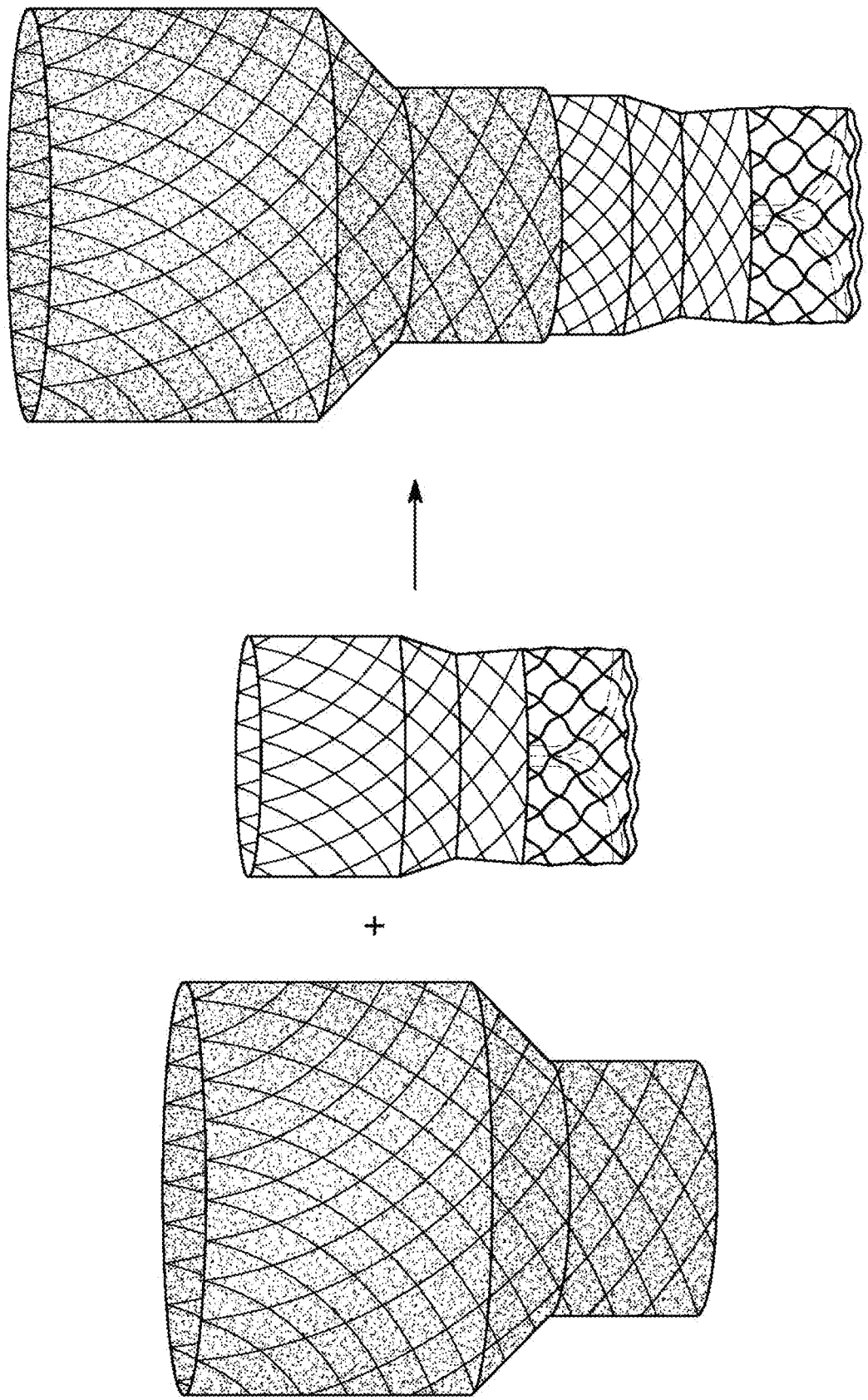
FIG. 10 is a front facing view of a modular transcatheter valve assembly with ascending repair component having a braided construction according to one or more embodiments described herein.

FIG. 10 illustrates the union of the proximal uncovered valve-bearing component and the distal covered component. This can be achieved by sliding one component into the other during the same procedure or at different procedure at different times. The valve element shows a "funnel" shape due to the expansive wire frame material at a top portion of the valve element. Once received within the main body, the valve element may compress to a more cylindrical shape. In this embodiment, the main section would be implanted first, and the valve section would be implanted second (as in many of the other embodiments disclosed herein). The open area of the valve section may define a larger grid or cell opening to allow for subsequent access for coronary repair.

Figure 11:
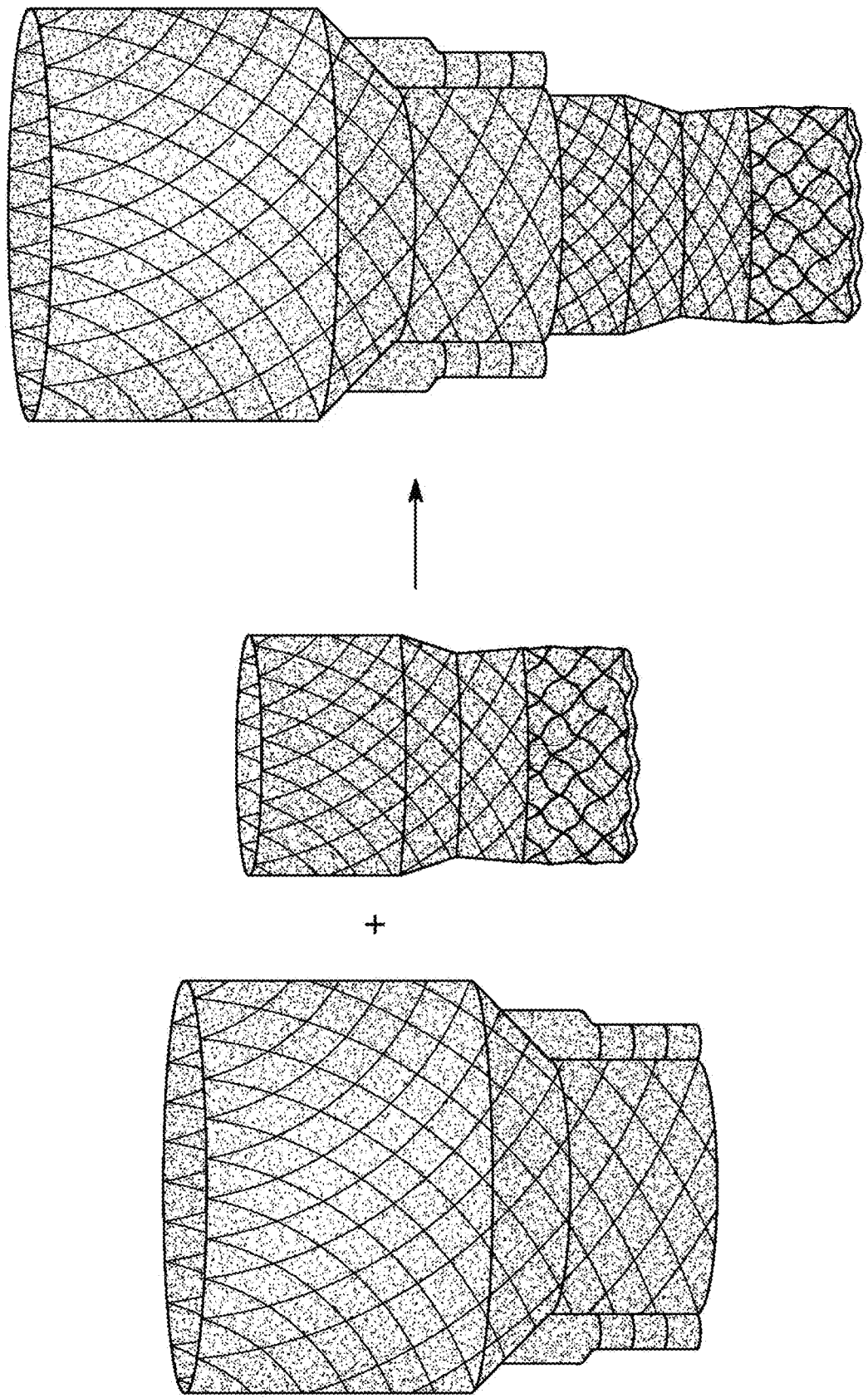
FIG. 11 is a front facing view of a modular transcatheter valve assembly with ascending repair component having a braided construction according to one or more embodiments described herein.

FIG. 11 illustrates the union of the proximal covered valve-bearing component and the distal covered component. This can be achieved by sliding one component into the other during the same procedure or at different procedure at different times. In this case the lateral conduits as described above provide access to and blood flow into the coronary arteries via connecting bridging stents.

Figure 12:
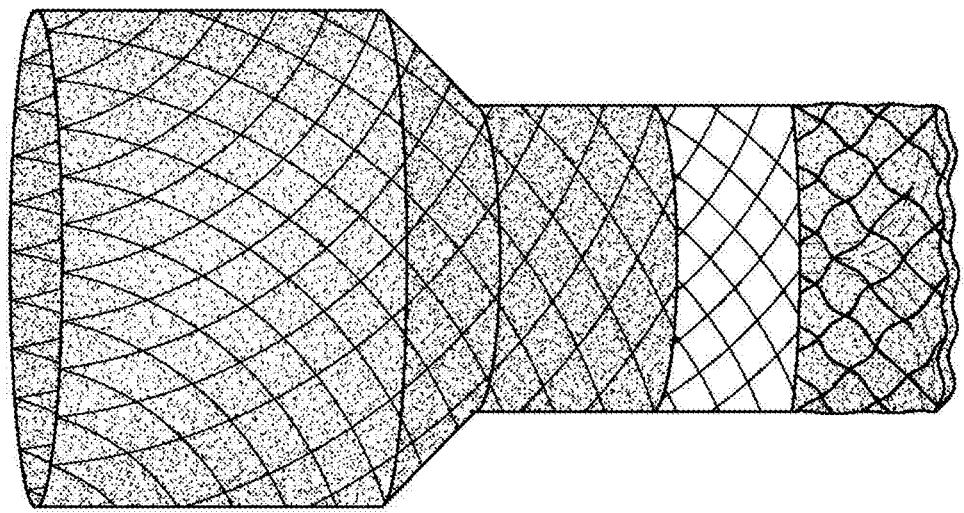
FIG. 12 is a front facing view of a modular transcatheter valve assembly with ascending repair component having a braided construction according to one or more embodiments described herein.
Figure 12:
Figure 12:
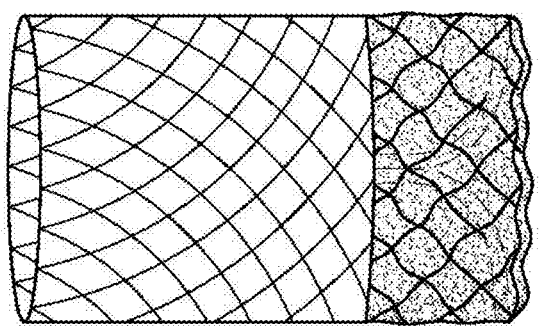
Figure 12:
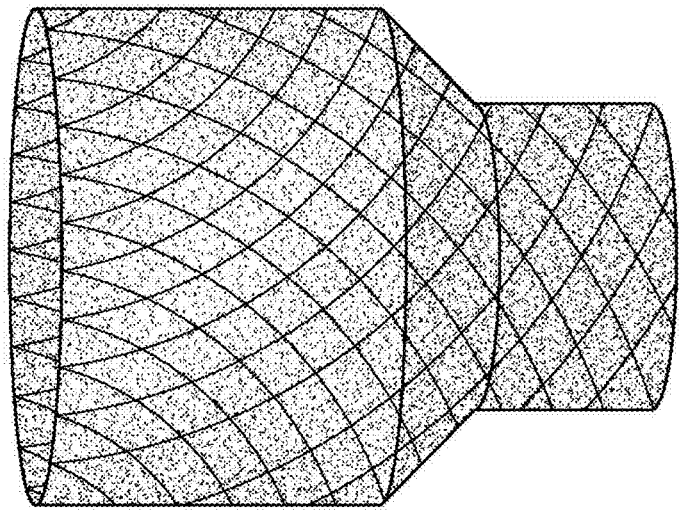

FIG. 12 illustrates the union of an at least partially uncovered proximal valve-bearing component and the distal covered component. This can be achieved by stitching or other mechanical, chemical or lamination methods, or through an interference fit by deploying the distal portion first and then the valved portion. The uncovered section of the proximal valve-bearing component is permeable and allows for direct blood flow into the coronary arteries.

Figure 13:
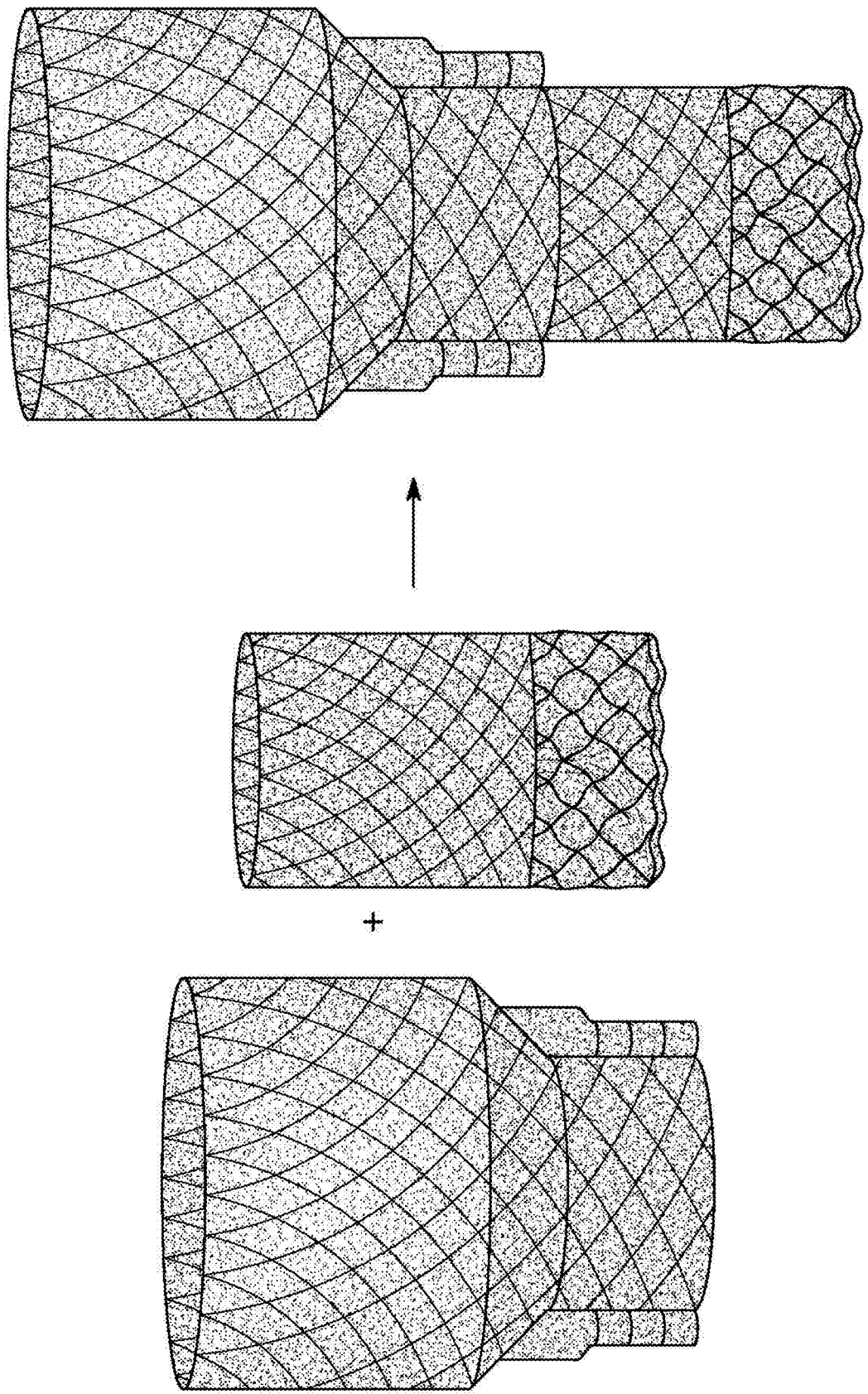
FIG. 13 is a front facing view of a modular transcatheter valve assembly with ascending repair component having a braided construction according to one or more embodiments described herein.

FIG. 13 illustrates the union of the proximal covered valve-bearing component and the distal covered component. This can be achieved by stitching or other mechanical, chemical or lamination methods. This can be achieved by sliding one component into the other during the same procedure or at different procedure at different times. In this case the lateral conduits as described above provide access to and blood flow into the coronary arteries via connecting bridging stents.

Figure 14:
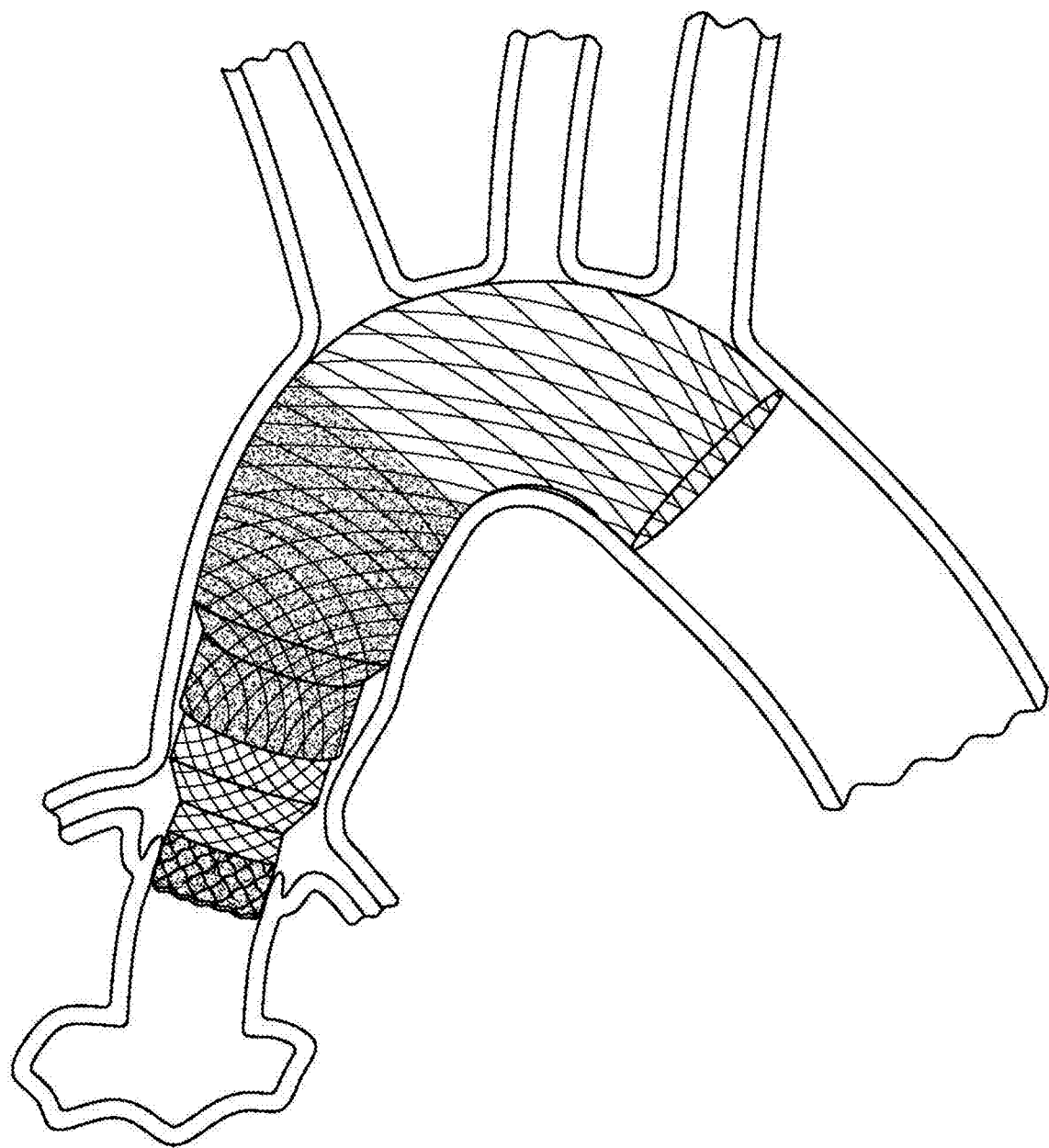
FIG. 14 is a side view of a modular transcatheter valve assembly with ascending repair and arch repair components having a braided construction according to one or more embodiments described herein.

FIG. 14 illustrates a device implanted in situ with a partially uncovered valve-bearing component slidably sealing against the partially uncovered distal component. The distal component is sealing against the aortic wall proximal to the innominate artery, where the distal uncovered section spans the arch to provide stability while maintaining blood flow to the supra-aortic vessels. The braided portion can have a smaller than illustrated grid or open cell configuration aimed at shielding emboli that may fracture from the valved component during implant. In this manner, the emboli would continue to travel towards kidneys for filtering by the body.

Figure 15:
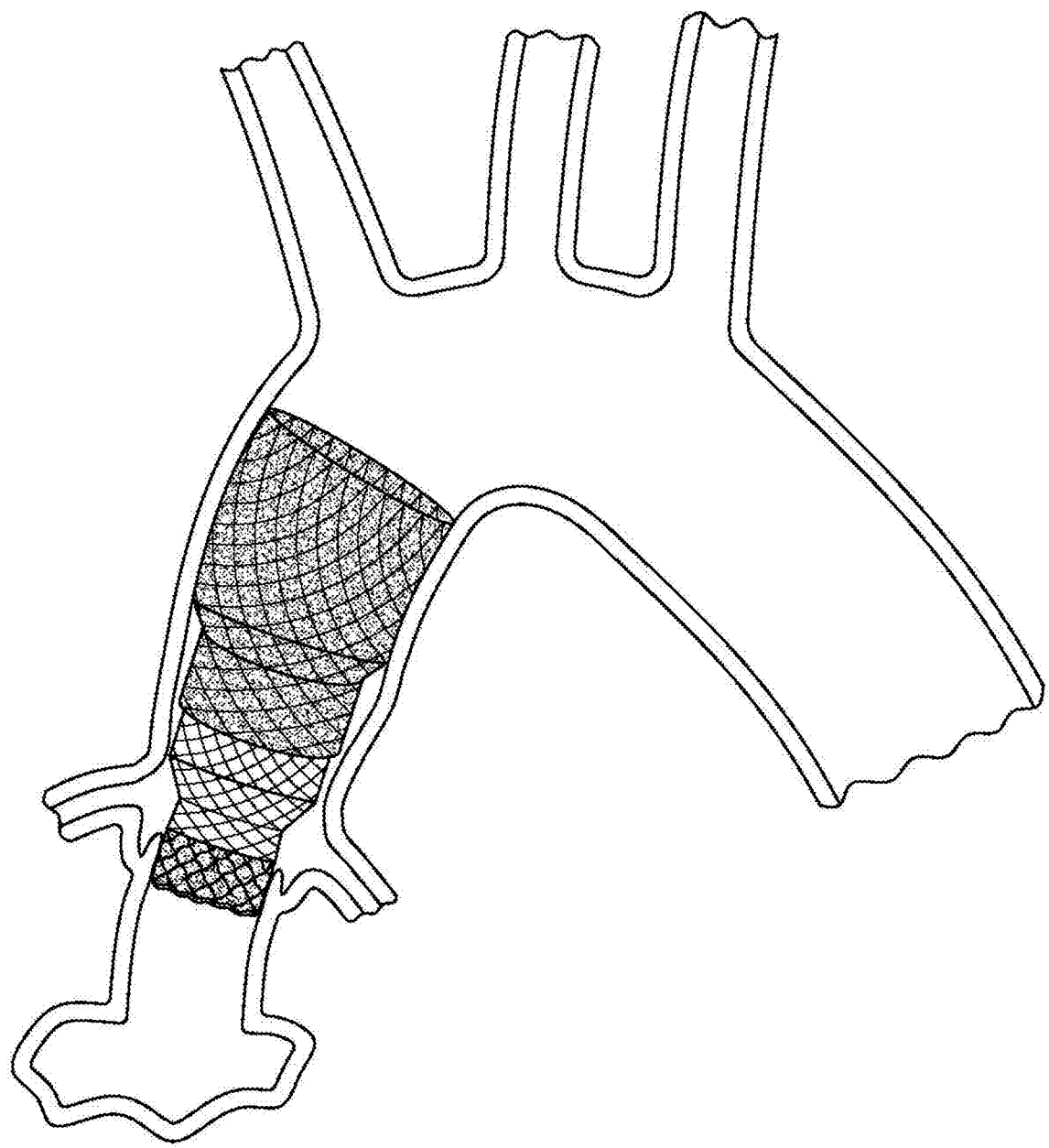
FIG. 15 is a side view of a modular transcatheter valve assembly with an ascending repair component having a braided construction according to one or more embodiments described herein.

FIG. 15 illustrates the device of FIG. 14, but the device does not include the uncovered arch section. The device terminates at the annulus before the supra-aortic arteries.

Figure 16:
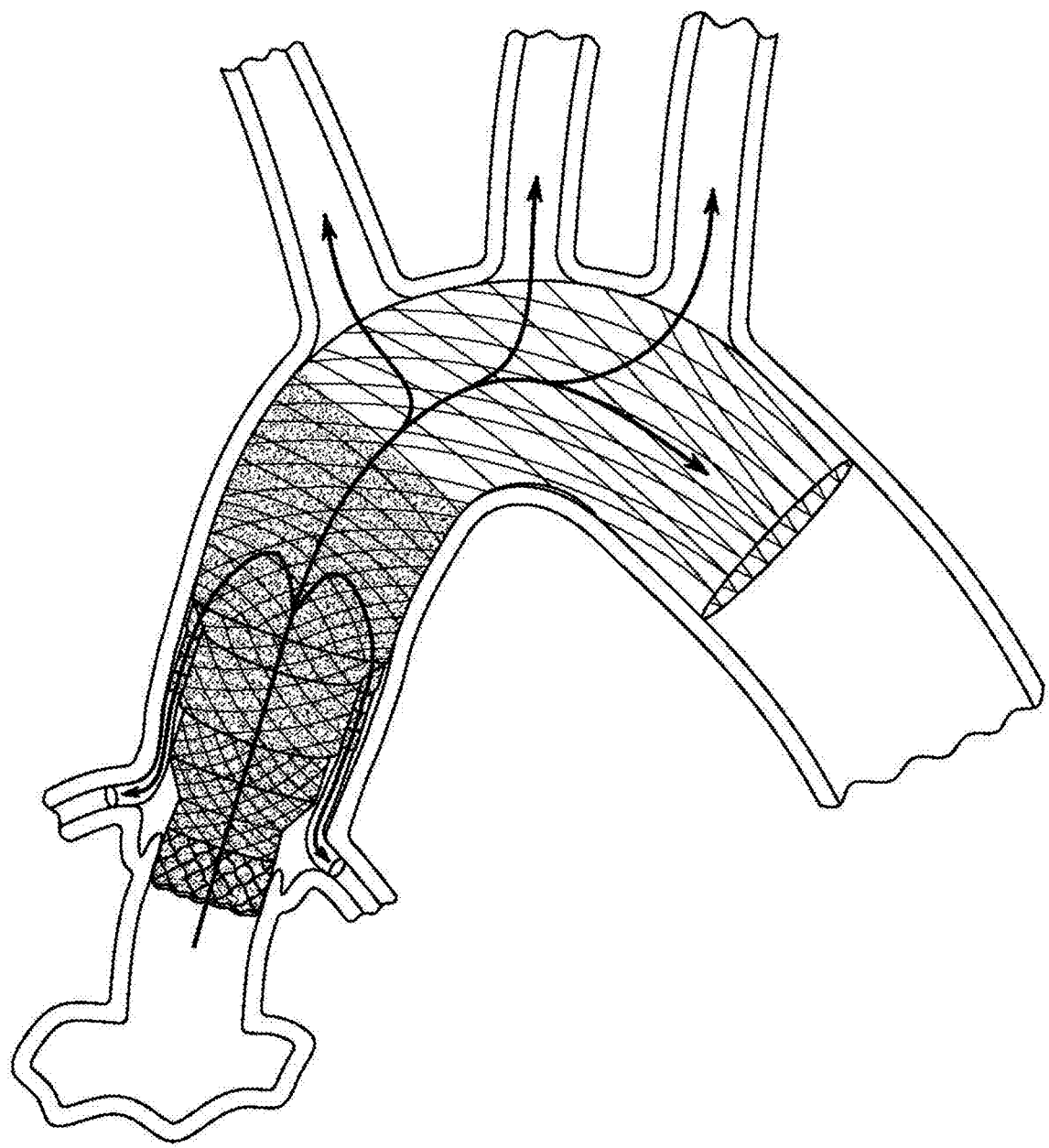
FIG. 16 is a side view of a modular transcatheter valve assembly with ascending repair and arch repair components having a braided construction according to one or more embodiments described herein.

FIG. 16 illustrates the device of FIG. 14 but the proximal valve-bearing component is impermeable and the coronary blood flow is supplied via the lateral conduits and bridging stents.

Figure 17:
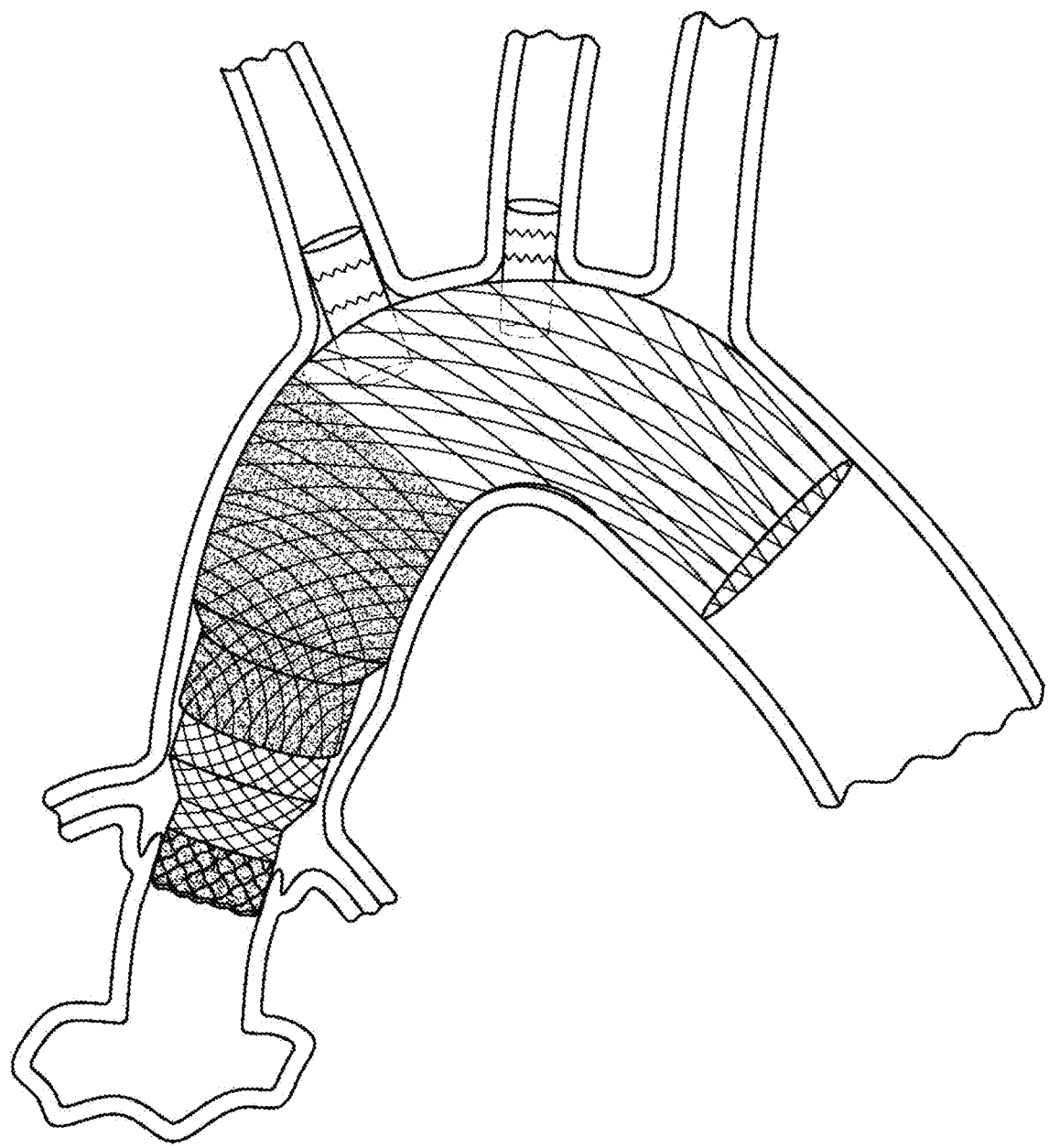
FIG. 17 is a side view of a modular transcatheter valve assembly with ascending repair and arch repair components having a braided construction according to one or more embodiments described herein.

FIG. 17 shows how the modular device shown in FIG. 14 can have a sealing interphase with a branched arch device or other arch devices via a sliding seal component for a complete ascending and arch repair. In this image the coronary blood flow is supplied directly from the uncovered section of the proximal component however is a combination with a fully covered and impermeable proximal component, the lateral conduits shown in other images can be used to supply coronary blood flow.

Figure 18:
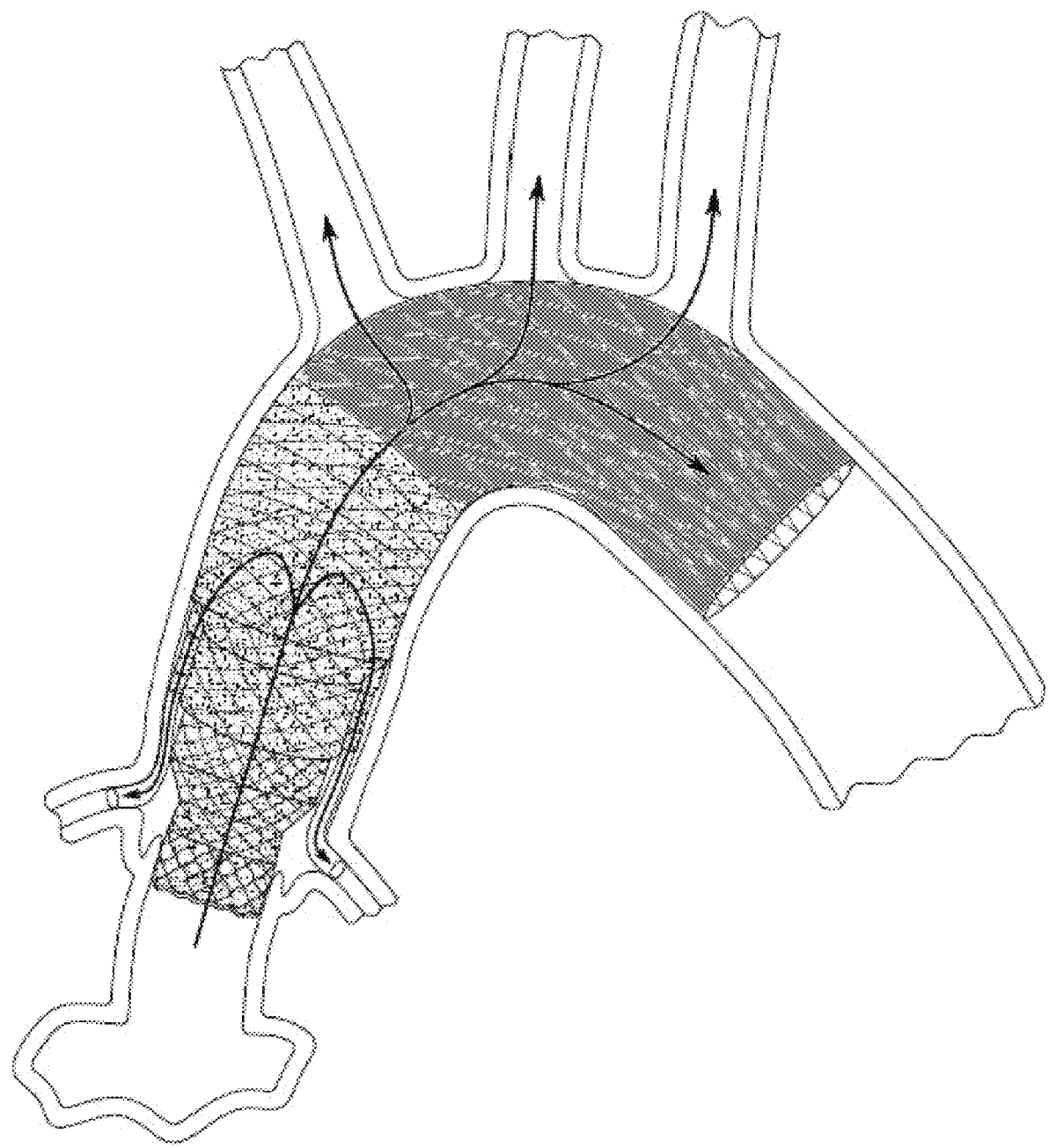
FIG. 18 illustrates an endovascular heart repair assembly that includes a proximal stent that defines a braided stent frame having a proximal end and a distal end and a valve housing at the proximal end of the transcatheter valve assembly.

FIG. 18 illustrates an endovascular heart repair assembly that includes a proximal stent that defines a braided stent frame having a proximal end and a distal end and a valve housing at the proximal end of the transcatheter valve assembly. A distal stent defines an uncovered portion that is configured to span supra-aortic arteries of the patient. The distal stent defining an open cell construction configured for passing blood flow into the supra-aortic arches and restricting flow through into the supra-aortic arteries embolic material greater than a predetermined diameter. In one or more embodiments, the open cell configuration has a pore size of between 40 micros and about 300 microns. In one or more embodiments, the open cell configuration has a pore size of between 100 and 200 microns.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

What is claimed:

1. A transcatheter valve and arch repair stent assembly, comprising:
    a transcatheter valve comprising:
        a main body that defines a braided stent frame having a proximal end and a distal end, wherein the braided stent frame is uncovered by a graft covering;
        a medial portion that defines an open facing surface that is configured to be positioned proximal coronary arteries of a patient when the transcatheter valve is deployed, wherein the medial portion is connected to the proximal end of the main body,
        wherein the open facing surface is formed from a gridded construction and is configured to allow the medial portion to be in fluid communication with the coronary arteries,
        wherein the medial portion defines a tapering or reduced diameter to provide clearance external to the transcatheter valve; and
        a valve housing connected to a proximal end of the medial portion,
        wherein the valve housing has a prosthetic valve leaflet assembly therein,
        wherein the main body, medial portion, and valve housing are pre-connected prior to implantation and the transcatheter valve is configured to be deployed within the patient in a single step; and
    an arch repair stent comprising:
        a proximal portion having a graft covering thereon; and
        an open cell portion is formed from a braided construction and is configured to span three arteries coupled to an aortic arch of the patient when the arch repair stent is deployed across the aortic arch,
        wherein the main body of the transcatheter valve is configured to be received within the proximal portion of the arch repair stent.

2. The transcatheter valve and arch repair stent assembly of claim 1, wherein the braided stent frame comprises a plurality of braided stent wires.

3. The transcatheter valve and arch repair stent assembly of claim 1, wherein the valve housing defines a wire frame having a graft material covering thereon.

4. The transcatheter valve and arch repair stent assembly of claim 1, wherein the main body is self expanding.

5. The transcatheter valve and arch repair stent assembly of a claim 1, wherein the valve housing is one of self expandable, self expandable in response to being unsheathed, or expandable in response to a balloon expansion.

* * * * *